(12) United States Patent
Canady et al.

(10) Patent No.: US 9,999,462 B2
(45) Date of Patent: Jun. 19, 2018

(54) INTEGRATED COLD PLASMA AND HIGH FREQUENCY PLASMA ELECTROSURGICAL SYSTEM AND METHOD

(71) Applicants: Jerome Canady, Lakeland, FL (US); Alexey Shashurin, West Lafayette, IN (US); Michael Keidar, Baltimore, MD (US); Taisen Zhuang, Vianna, VA (US)

(72) Inventors: Jerome Canady, Lakeland, FL (US); Alexey Shashurin, West Lafayette, IN (US); Michael Keidar, Baltimore, MD (US); Taisen Zhuang, Vianna, VA (US)

(73) Assignee: U.S. Patent Innovations, LLC, Takoma Park, MD (US)

( * ) Notice: Subject to any disclaimer, the term of this patent is extended or adjusted under 35 U.S.C. 154(b) by 169 days.

(21) Appl. No.: 14/725,167

(22) Filed: May 29, 2015

(65) Prior Publication Data
US 2015/0342663 A1 Dec. 3, 2015

Related U.S. Application Data

(60) Provisional application No. 62/004,360, filed on May 29, 2014.

(51) Int. Cl.
*A61B 18/12* (2006.01)
*A61B 18/04* (2006.01)
(Continued)

(52) U.S. Cl.
CPC ........ *A61B 18/1206* (2013.01); *A61B 18/042* (2013.01); *A61B 2018/00172* (2013.01);
(Continued)

(58) Field of Classification Search
CPC .............. A61B 18/042; A61B 18/0206; A61B 2018/00172; A61B 2018/00178;
(Continued)

(56) References Cited

U.S. PATENT DOCUMENTS

| 4,040,426 A | 8/1977 | Morrison |
| 4,429,694 A | 2/1984 | McGreevy |

(Continued)

FOREIGN PATENT DOCUMENTS

WO 2012061535 A2 5/2012

OTHER PUBLICATIONS

A. Erwine, "ESU-2000 Series Product Overview A Paradigm Shift in Electrosurdery Testing Technology and Capability is Here," BC Group International, Inc. (2007).

(Continued)

*Primary Examiner* — Joseph Stoklosa
*Assistant Examiner* — Tigist Demie
(74) *Attorney, Agent, or Firm* — 24IP Law Group; Timothy R DeWitt

(57) ABSTRACT

A system that does conversion from regular hot plasma produced by ESU to cold plasma which is thermally harmless for the tissue. The system is comprised of Conversion Unit and Cold Plasma Probe. Output signal for ESU connects to CU along with Helium flow. The CU converts signal from ESU and send it to the output connector along with helium flow. Cold Plasma Probe is connected directly to the CU output. At the end of the CPP probe cold plasma is produced.

18 Claims, 6 Drawing Sheets

(51) Int. Cl.
*A61B 18/00* (2006.01)
*H05H 1/46* (2006.01)
(52) U.S. Cl.
CPC ............... *A61B 2018/00178* (2013.01); *A61B 2018/00583* (2013.01); *H05H 2001/4682* (2013.01); *H05H 2245/122* (2013.01)
(58) Field of Classification Search
CPC .......... A61B 2018/00583; A61B 18/14; A61B 2018/1286; H05H 2245/122; H05H 1/46; H05H 2001/466; H05H 2001/4682; C12N 13/00
See application file for complete search history.

(56) References Cited

U.S. PATENT DOCUMENTS

| | | | |
|---|---|---|---|
| 4,781,175 | A | 11/1988 | McGreevy |
| 5,088,997 | A | 2/1992 | Delahuerga et al. |
| 5,098,430 | A | 3/1992 | Fleenor |
| 5,207,675 | A | 5/1993 | Canady |
| 5,217,457 | A | 6/1993 | Delahuerga et al. |
| 6,149,648 | A | 11/2000 | Cosmescu |
| 7,517,347 | B2 | 4/2009 | Hug et al. |
| 2006/0052774 | A1 | 3/2006 | Garrison |
| 2006/0122595 | A1 | 6/2006 | Farin |
| 2007/0225699 | A1 | 9/2007 | Goble |
| 2010/0145253 | A1* | 6/2010 | Gutsol .................. A61B 18/042 604/20 |
| 2013/0237982 | A1* | 9/2013 | Rencher ............. A61B 18/1402 606/39 |

OTHER PUBLICATIONS

"Force Argon II System," Valleylab 2006.
"Argon-Plasma Koagulation," GMS Krankenhaushygiene Interdisziplinär 2008, vol. 3(1), ISSN 1863-5245.
"Valleylab Force Argon II Argon Enhanced Electrosurgical System," 1997.
A. Fridman, Plasma Chemistry (Cambridge University Press, 2008).
G. Fridman, G. Friedman, A. Gutsol, A. B. Shekhter, V. N. Vasilets, and A. Fridman "Applied Plasma Medicine," Plasma Processes Polym. 5, 503 (2008).
E. Stoffels, Y. Sakiyama, and D.B. Graves "Cold Atmospheric Plasma: Charged Species and Their Interactions With Cells and Tissues," IEEE Trans. Plasma Sci. 36, 1441 (2008).
X. Lu, Y. Cao, P. Yang, Q. Xiong, Z. Xiong, Y. Xian, and Y. Pan "An RC Plasma Device for Sterilization of Root Canal of Teeth," IEEE Trans. Plasma Sci. 37, 668 (2009).
K.H. Becker, K.H. Shoenbach and J.G. Eden "Microplasma and applications," J. Phys. D.:Appl.Phys. 39, R55-R70 (2006).
E. Stoffels, I.E Kieft, R.E.J Sladek, L.J.M van den Bedem, E.P van der Laan, M. Steinbuch "Plasma needle for in vivo medical treatment: recent developments and perspectives," Plasma Sources Sci. Technol. 15, S169-S180 (2006).
M. Keidar, A. Shashurin, R. Ravi, R. Guerrero-Preston and B. Trink, British Journal of Cancer 105, 1295 (2011).
A. Shashurin, M.Keidar, S.Bronnikov, R.A. Jurjus, M.A. Stepp, Appl.Phys.Let. 92, 181501 (2008).
A. Shashurin, M.A. Stepp, T.S. Hawley, S. Pal-Ghosh, L. Brieda, S. Bronnikov, R.A. Jurjus, M. Keidar, "Influence of cold plasma atmospheric jet on integrin activity of living cells," Plasma Process. Polym. 7 294 (2010).
O. Volotskova, T. S. Hawley, M. A. Stepp & M. Keidar, "Targeting the cancer cell cycle by cold atmospheric plasma," Scientific Reports, 2:636, Sep. 6, 2012.
Maynard, J.E., "Tuned Transformers . . . Design of these electronic units simplified by means of universal performance curves," General Electric Review, Oct. 1943 pp. 559-609.
Huffman, B., "Parasitic Capacitance Effects in Step-up Transformer Design," Linear Technology, Application Note 39, Feb. 1990.
Transformer and Inductor Design Handbook, Chapter 17 (2004).

\* cited by examiner

INTEGRATED COLD PLASMA AND HIGH FREQUENCY PLASMA ELECTROSURGICAL SYSTEM AND METHOD

CROSS-REFERENCE TO RELATED APPLICATIONS

The present application claims the benefit of the filing date of U.S. Provisional Patent Application Ser. No. 62/004,360 filed by the present inventors on May 29, 2014.

The aforementioned provisional patent application is hereby incorporated by reference in its entirety.

STATEMENT REGARDING FEDERALLY SPONSORED RESEARCH OR DEVELOPMENT

None.

BACKGROUND OF THE INVENTION

Field of the Invention

The present invention relates to a systems for producing cold plasmas.

Background of the Related Art

The unique chemical and physical properties of cold atmospheric plasmas enable their numerous recent applications in biomedicine including sterilization, the preparation of polymer materials for medical procedures, wound healing, tissue or cellular removal and dental drills. A. Fridman, Plasma Chemistry (Cambridge University Press, 2008); G. Fridman, G. Friedman, A. Gutsol, A. B. Shekhter, V. N. Vasilets, and A. Fridman "Applied Plasma Medicine", *Plasma Processes Polym.* 5, 503 (2008); E. Stoffels, Y. Sakiyama, and D. B. Graves "Cold Atmospheric Plasma: Charged Species and Their Interactions With Cells and Tissues" *IEEE Trans. Plasma Sci.* 36, 1441 (2008); X. Lu, Y. Cao, P. Yang, Q. Xiong, Z. Xiong, Y. Xian, and Y. Pan "An RC Plasma Device for Sterilization of Root Canal of Teeth" *IEEE Trans. Plasma Sci.* 37, 668 (2009).

Plasma-based nitrogen oxide (NO) therapy demonstrated huge potential for stimulation of regenerative processes and wound healing. The work uncovering function of nitrogen oxide as a signal molecule was awarded by the Nobel Prize in medicine and biology in 1999. NO-therapy demonstrated tremendous effect of acceleration of healing of ulcer, burns and serious wounds. Other experimental evidence supports efficiency of cold plasmas produced by dielectric barrier discharge for apoptosis of melanoma cancer cell lines, treatment of cutaneous leishmaniasis, ulcerous eyelid wounds, corneal infections, sterilization of dental cavities, skin regeneration, etc.

Recent progress in atmospheric plasmas led to creation of cold plasmas with ion temperatures close to room temperature. Cold non-thermal atmospheric plasmas can have tremendous applications in biomedical technology. K. H. Becker, K. H. Shoenbach and J. G. Eden "Microplasma and applications" *J. Phys. D.: Appl. Phys.* 39, R55-R70 (2006). In particular, plasma treatment can potentially offer a minimum-invasive surgery that allows specific cell removal without influencing the whole tissue. Conventional laser surgery is based on thermal interaction and leads to accidental cell death i.e. necrosis and may cause permanent tissue damage. In contrast, non-thermal plasma interaction with tissue may allow specific cell removal without necrosis. In particular, these interactions include cell detachment without affecting cell viability, controllable cell death etc. It can be used also for cosmetic methods of regenerating the reticular architecture of the dermis. The aim of plasma interaction with tissue is not to denaturate the tissue but rather to operate under the threshold of thermal damage and to induce chemically specific response or modification. In particular presence of the plasma can promote chemical reaction that would have desired effect. Chemical reaction can be promoted by tuning the pressure, gas composition and energy. Thus the important issues are to find conditions that produce effect on tissue without thermal treatment. Overall plasma treatment offers the advantage that is can never be thought of in most advanced laser surgery. E. Stoffels, I. E Kieft, R. E. J Sladek, L. J. M van den Bedem, E. P van der Laan, M. Steinbuch "Plasma needle for in vivo medical treatment: recent developments and perspectives" *Plasma Sources Sci. Technol.* 15, S169-S180 (2006).

In recent few years cold plasma interaction with tissues becomes very active research topic due to aforementioned potential. Preliminary experiments have demonstrated potent effects of cold plasma treatment on cancerous tissue both in vitro and in vivo and suggest the important role of the reactive oxygen species (ROS) in the selective treatment of cancer. In-vivo efficiency of cold plasmas for ablation of mid-sized subcutaneous bladder cancer tumors on mice was demonstrated. M. Keidar, A. Shashurin, R. Ravi, R. Guerrero-Preston and B. Trink, *British Journal of Cancer* 105, 1295 (2011). Also, selectivity of plasmas for killing of cancerous cells while remaining healthy cells intact was demonstrated in vitro for various cell lines. Cellular level effects include detachment of cells from extracellular matrix and decreasing of migration velocity of cells, while the sub-cellular level effect is the reduction of cell surface integrin expression (receptors responsible for cell adhesion and migration). A. Shashurin, M. Keidar, S. Bronnikov, R. A. Jurjus, M. A. Stepp, *Appl. Phys. Let.* 92, 181501 (2008). A. Shashurin, M. A. Stepp, T. S. Hawley, S. Pal-Ghosh, L. Brieda, S. Bronnikov, R. A. Jurjus, M. Keidar, Influence of cold plasma atmospheric jet on integrin activity of living cells *Plasma Process. Polym.* 7 294 (2010). In addition, it was found that normal and cancer cells respond to CAP differently depending on the where they are in terms of the cell cycle through their various life functions. Migration of normal cells was reduced by 30% ($p<0.001$), however the cancer cells react differently: more aggressive carcinoma cells showed more response in the decrease of the migration rates (~20% with $p<0.001$) than less aggressive papilloma cells ($p>0.05$). It was also found that CAP induces a transient 2-fold G2/M-arrest in papilloma and carcinoma cells; normal epithelial cells did not show any change in cell cycle progression. O. Volotskova, T. S. Hawley, M. A. Stepp & M. Keidar, "Targeting the cancer cell cycle by cold atmospheric plasma," *Scientific Reports,* 2:636, Sep. 6, 2012

Given these findings, cold plasma represents a promising new adjunct for cancer therapy, offering the ability to directly target and selectively kill cancerous cells. CAP can lead to a new paradigm in cancer therapy by offering a minimum-invasive surgery technique that allows specific cell removal without affecting the whole tissue. CAP demonstrated in-vitro and in-vivo highly selective potential towards number of cancer cell line (lung, bladder, head & neck, skin etc.) and, as such, has potential to address limitations of current clinical chemotherapeutic approaches contain with regards to nonselective and incomplete tumor ablation. In addition, CAP action leads to selective decrease in cancer cell migration, thus has potential to mitigate the metastasis and may lead to the development of a novel therapeutic approach for metastasis.

A variety of different electrosurgical generators are known. U.S. Pat. No. 4,429,694 to McGreevy disclosed an electrosurgical generator and argon plasma system and a variety of different electrosurgical effects that can be achieved depending primarily on the characteristics of the electrical energy delivered from the electrosurgical generator. The electrosurgical effects included pure cutting effect, a combined cutting and hemostasis effect, a fulguration effect and a desiccation effect. Fulguration and desiccation sometimes are referred to collectively as coagulation.

Another method of monopolar electrosurgery via argon plasma technology was described by Morrison in U.S. Pat. No. 4,040,426 in 1977 and McGreevy U.S. Pat. No. 4,781,175. This method, referred to as argon plasma coagulation (APC) or argon beam coagulation is a non-contact monopolar thermoablative method of electrocoagulation that has been widely used in surgery for the last twenty years. In general, APC involves supplying an ionizable gas such as argon past the active electrode to target tissue and conducting electrical energy to the target tissue in ionized pathways as non-arcing diffuse current. Canady described in U.S. Pat. No. 5,207,675 the development of APC via a flexible catheter that allowed the use of APC in endoscopy. These new methods allowed the surgeon, endoscopist to combine standard monopolar electrocautery with a plasma gas for coagulation of tissue.

Yet another system is disclosed in WO 2012/061535 A2, which disclosed a system for simultaneously cutting and coagulating tissue.

SUMMARY OF THE INVENTION

The present invention relates to the system comprised of two units namely Conversion Unit (CU) and Cold Plasma Probe (CPP). The CU is connected to an electrosurgical generator (ESU) output and does conversion of the ESU signal. The CPP is connected to the CU output. At the end of the CPP cold plasma is produced and is thermally harmless to living tissue, i.e., it cannot cause burns to the tissue. This cold plasma, however, is deadly for cancer cells while leaving normal cells unaffected.

It is an object of the invention to provide a system for producing cold plasma. The system includes Conversion Unit and Cold Plasma Probe.

CU is connected directly to an electrosurgical unit. The CPP is connected to the CU output. Cold plasma is produced at the distal end of the CPP. The connection schematics are shown in FIG. 1.

Still other aspects, features, and advantages of the present invention are readily apparent from the following detailed description, simply by illustrating a preferable embodiments and implementations. The present invention is also capable of other and different embodiments and its several details can be modified in various obvious respects, all without departing from the spirit and scope of the present invention. Accordingly, the drawings and descriptions are to be regarded as illustrative in nature, and not as restrictive. Additional objects and advantages of the invention will be set forth in part in the description which follows and in part will be obvious from the description, or may be learned by practice of the invention.

BRIEF DESCRIPTION OF THE FIGURES

For a more complete understanding of the present invention and the advantages thereof, reference is now made to the following description and the accompanying drawings, in which.

DETAILED DESCRIPTION OF THE PREFERRED EMBODIMENT

Figure 1:
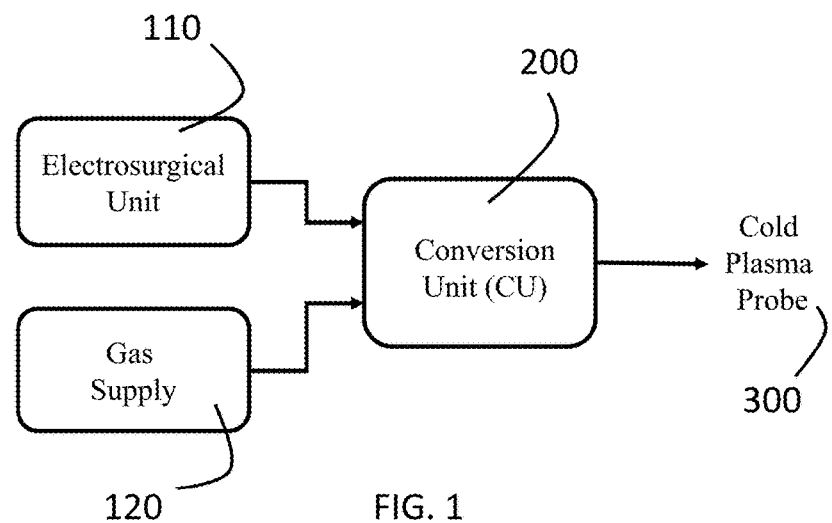
FIG. 1 is a diagram of a system for producing cold plasmas in accordance with a preferred embodiment of the invention.

In describing a preferred embodiment of the invention illustrated in the drawings, specific terminology will be resorted to for the sake of clarity. However, the invention is not intended to be limited to the specific terms so selected, and it is to be understood that each specific term includes all technical equivalents that operate in similar manner to accomplish a similar purpose. The preferred embodiment of the invention is described for illustrative purposes, it being understood that the invention may be embodied in other forms not specifically shown in the drawings.

The present invention produces cold plasmas which are thermally harmless for the living biological tissue and cannot cause burns. The cold plasma produced by the present invention, however, is deadly for cancer cells while leaving normal cells unaffected.

Figure 2:
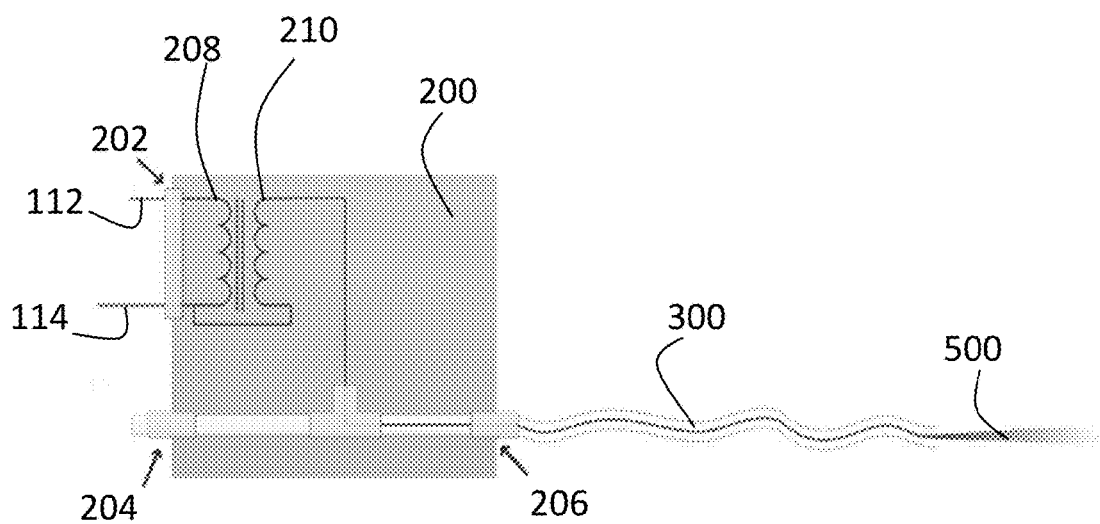
FIG. 2 is a diagram of a Conversion Unit (CU) and Cold Plasma Probe (CPP) in accordance with a preferred embodiment of the present invention.

The conversion unit (CU) 200 is equipped with 3 connectors, namely a gas connector 204 (to helium tank 120), an electrical connector 202 (to electrosurgical unit 110) and an electro-gas connector 206 (to cold plasma probe 300) as shown in FIG. 2.

The gas connector 204 is an input connection. It connects an inert gas such as Helium tank 120 to the CU 200 and delivers the inert gas to the CU. For example, different grades of the Helium can be used to the helium tank. Flow rates less than 1-15 L/min should be used.

The electrical connector 202 is an input connection. It connects between the ESU 110 and the CU 200 and delivers power to the CU 200. A high voltage output 112 of the ESU and a patient output 114 of the ESU 110 are used as inputs to the CU 200.

The electro-gas connector 206 is the output of the CU 200 and is connected to the cold plasma probe (CPP) 300. The electro-gas connector 206 supplies an output electrical signal and helium to the cold plasma probe.

Figure 3A:
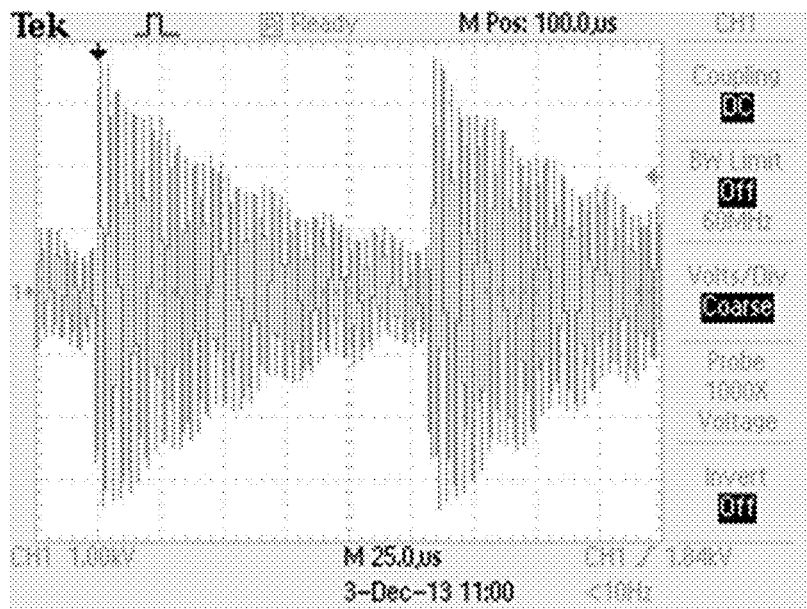
FIGS. 3A and 3B show converted waveforms output from a CU in accordance with a preferred embodiment of the present invention.
Figure 3B:
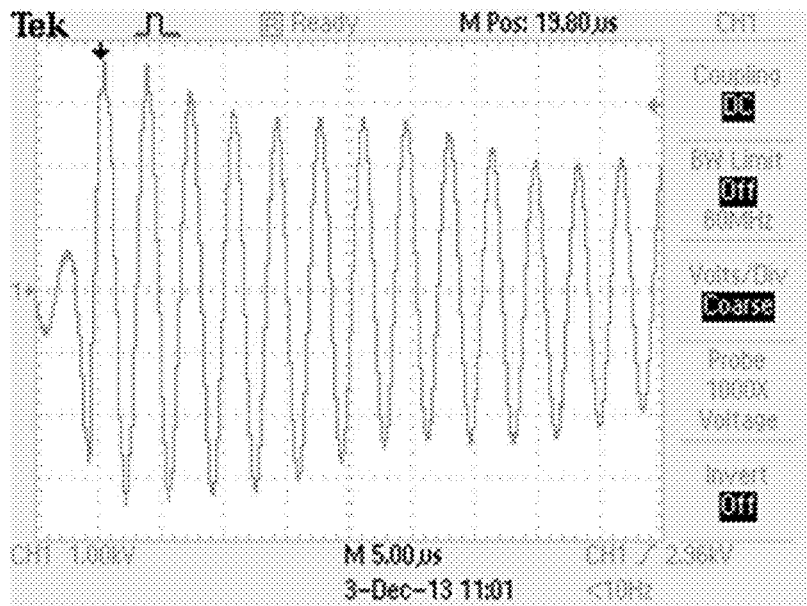
Figure 4:
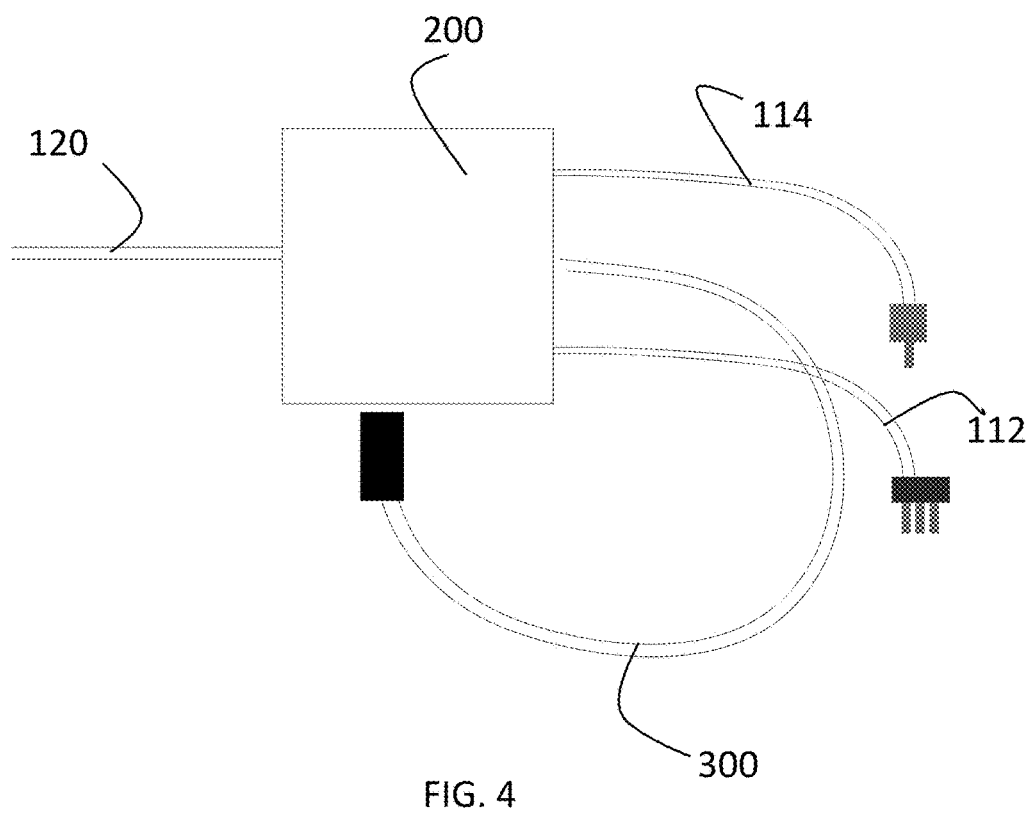
FIG. 4 is an illustrations of a CU with attached CPP in accordance with a preferred embodiment of the present invention.

The CU 200 utilizes a high voltage transformer connected to output from ESU 110 as shown in FIG. 2. In a preferred embodiment, the transformer utilizes a primary coil 208 with $N_1$=60-70 turns and secondary coil 210 with about $N_2$=300 turns. The coils are wound on a ferrite core. The specific number of turns utilized in the transformer is given for illustrative purpose only and can be varied in a very wide range. The number $N_2$ should be larger than $N_1$ in order to produce step-up conversion of the voltage. The CU output waveform in the preferred embodiment is shown in FIG. 3.

The CU up-converts voltage. In the preferred embodiment voltage of about 4 kV is produced. Other embodiments of the CU can be used to up-convert the voltage. The output voltage of the CU should be in a range 1.5-50 kV.

The CU down-converts frequency. In the preferred embodiment frequency about 295 kHz is produced. Other embodiments of the CU can be used to down-convert the frequency. Outputted frequencies should be less than about 300 kHz.

The CU down-converts power. In the preferred embodiment, secondary coil can produce power <10 Watt. Other embodiments of the CU can be used to down-convert the frequency. The CU output power should not exceed 20-30 Watt.

A Cold Plasma Probe (CPP) 300 is connected to Electro-Gas output connector 206 of the CU. Probe length was about 0.5 meter in the preferred embodiment. However, the present invention is not limited solely to this CPP length, and probe can be up to 5-10 meters long. Output voltage of the transformer should be increased if longer probes are used.

The Cold Plasma Probe 300 is made of flexible tube and equipped with wire electrode. The probe 300 may have at its distal end a housing or other structure 310 for use in holding the distal end of the probe. Other structures such as handle may be used but are not necessary. Wire electrode in the preferred embodiment is located inside the tube. However, it can also be placed outside the tube.

The cold plasma 500 is triggered, for example, by pressing the foot pedal in Coagulation mode. Any Coagulation powers can be used, however increase of the Coagulation Power setting will result in brighter and more intense cold plasma In the preferred embodiment, CPP has no control buttons on it and cold plasma is turned on directly by pressing the foot pedal. However, CPP may be equipped with control buttons in order to ignite cold plasma and adjust helium flow by pressing buttons on the CPP itself.

Figure 5A:
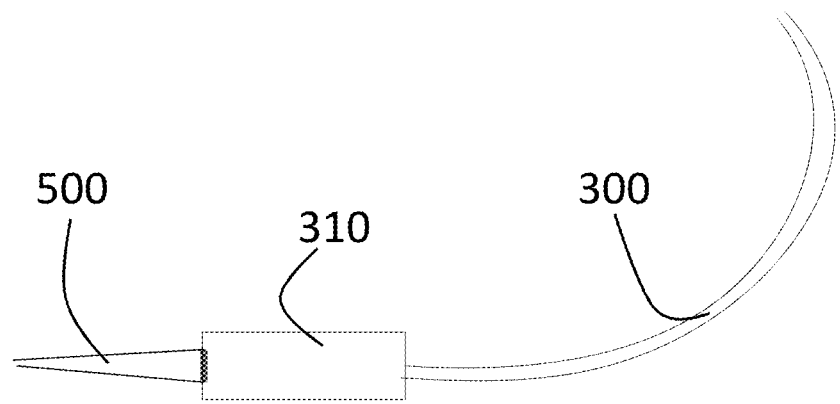
FIG. 5A is an illustration of free cold plasma generated in accordance with a preferred embodiment of the present invention.
Figure 5B:
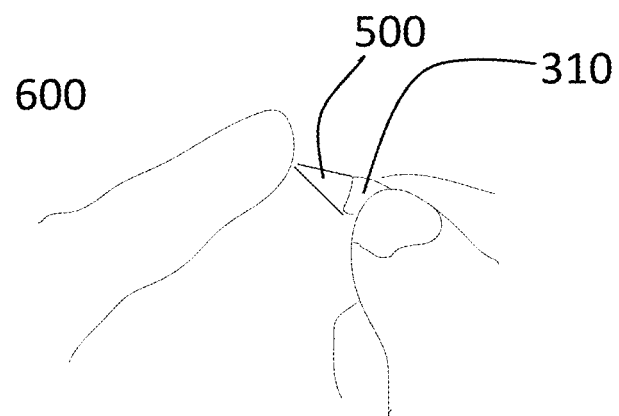
FIG. 5B is an illustration a cold plasma generated in accordance with a preferred embodiment of the present invention in contact with finger.
Figure 6:
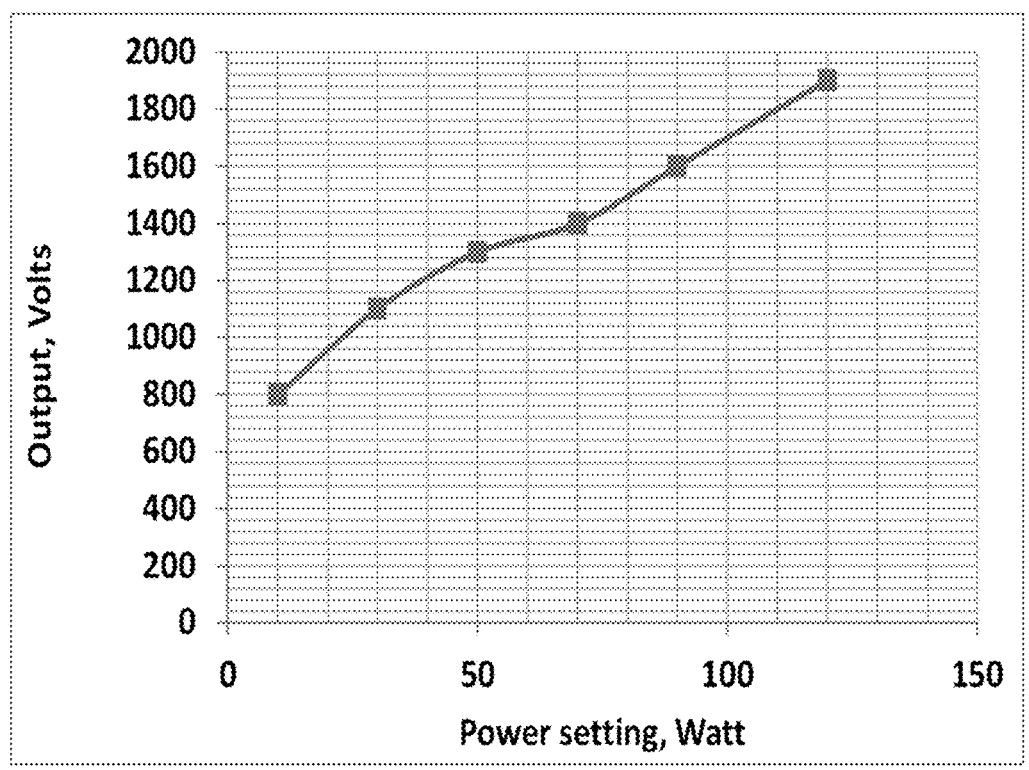
FIG. 6 is a graph of RMS output voltage of Conversion Unit vs. input power setting on an electrosurgical unit (ESU) unit.

The length of free cold plasma jet in experiments was up to 3-4 cm as shown in FIG. 5A. Placing finger into the cold plasma without any damage is shown in FIG. 5B.

EXAMPLE

The transformer in the CU utilizes primary coil with N1=30 turns of AWG 30 magnet wire and secondary coil with about N2=250 turns of AWG 36 magnet wire. Ferroxcube core UR64/40/20-3C90 was used. Insulation between the windings was up to 10 kV and between the windings to the core—up to 7 kV.

The Conversion Unit in this embodiment produced high voltage with RMS up to about 2 kV and frequency about 150 kHz. Power delivered into cold plasmas was <5 Watt. The dependence of RMS output voltage of Conversion Box vs. input power setting on ESU is show in FIG. 2.

Figure 8:
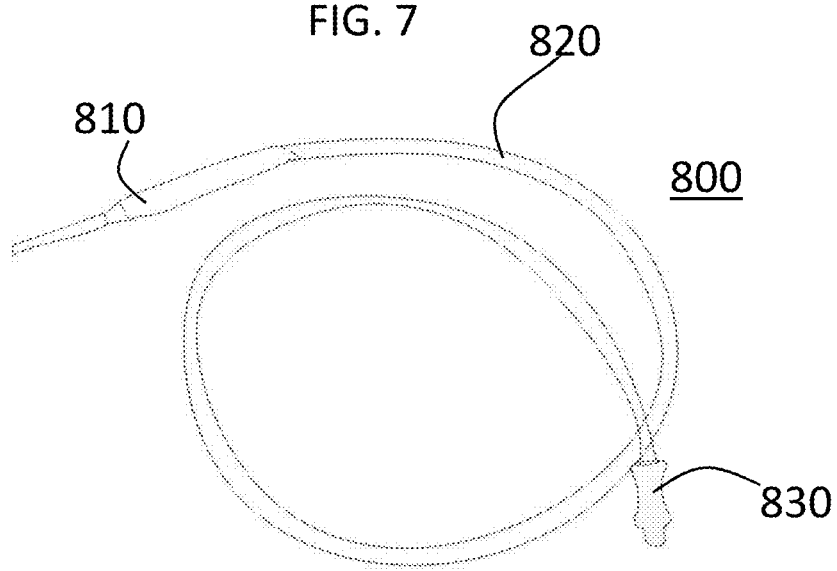
FIG. 8 is a schematic diagram of a Cold Plasma Probe (CPP) in accordance with another preferred embodiment of the present invention.

CPP shown in FIG. 8 can utilize one-electrode or two-electrode configuration. In one-electrode configuration—high voltage electrode can be placed inside the flexible tube used for the Helium supply or embedded in the tube's wall.

In two-electrode configuration high voltage electrode is placed inside the tube and grounded shield is embedded in the tube walls.

Figure 7:
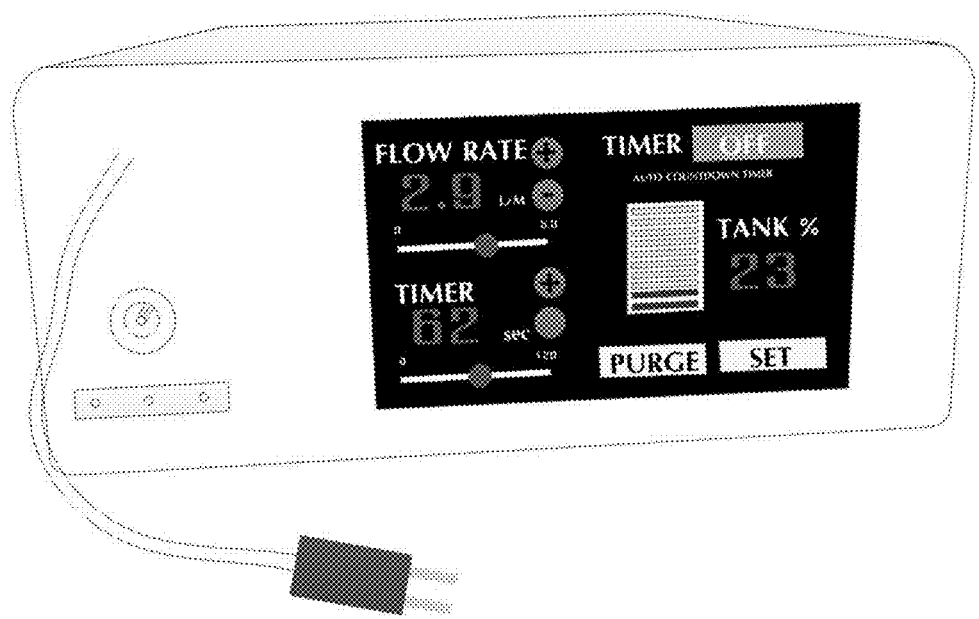
FIG. 7 is a diagram of a Conversion Unit in accordance with another preferred embodiment of the present invention.

The schematic view of the Conversion Box and 3 meter long Cold Plasma Probe are shown in FIGS. 7 and 8 respectively. Preferred Helium flow rate for this embodiment was about 5 LPM. The probe 800 has handle 810, an elongated tube 820 and a connector 830 for connecting the probe to the CU.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment was chosen and described in order to explain the principles of the invention and its practical application to enable one skilled in the art to utilize the invention in various embodiments as are suited to the particular use contemplated. It is intended that the scope of the invention be defined by the claims appended hereto, and their equivalents. The entirety of each of the aforementioned documents is incorporated by reference herein.

What is claimed is:

1. An electrosurgical apparatus comprising:
   a conversion unit comprising:
      a first connector adapted to connect said conversion unit to an electrosurgical generator;
      a high voltage transformer having a ferrite core, a primary coil of magnetic wire having a first diameter and a secondary coil of magnetic wire having a second diameter, the secondary coil having a larger number of turns than the primary coil and a said second diameter being smaller than said first diameter; and
      a second connector adapted to connect the conversion unit to a cold plasma probe;
   wherein said conversion unit receives electrical energy having a specific voltage, and frequency from said electrosurgical generator and up-converts the voltage, and down-converts the frequency of the electrical energy received from the electrosurgical generator.

2. An electrosurgical apparatus according to claim 1, further comprising a cold plasma probe connected to said second connector of said conversion unit.

3. An electrosurgical apparatus according to claim 1, wherein said second connector for connecting a cold plasma probe comprises an electro-gas output connector.

4. An electrosurgical apparatus according to claim 1, further comprising an electrosurgical generator, wherein said first connector for connecting said conversion unit to an electrosurgical generator connects to a high-voltage output of said electrosurgical generator and to a patient output of said electrosurgical generator.

5. An electrosurgical apparatus according to claim 3, wherein said conversion unit further comprises a gas connector for connecting said conversion unit to a source of an inert gas.

6. An electrosurgical apparatus comprising:
   a conversion unit comprising:
      a first connector for connecting said conversion unit to an electrosurgical generator;
      a high voltage transformer having a ferrite core, a primary coil of wire on said core and a secondary coil of wire on said core, said primary coil of wire having a first gauge and said secondary coil of wire having a second gauge, the secondary coil having a larger number of turns than the primary coil and said second gauge being smaller than said first gauge; and a second connector for connecting the conversion unit to a cold plasma probe.

7. An electrosurgical apparatus according to claim 6, wherein said conversion unit receives electrical energy having a first voltage and first frequency from an electrosurgical generator through said first connector and outputs through said second connector electrical energy having a second voltage and second frequency, said second voltage being greater than said first voltage and said second frequency being less than said first frequency.

8. An electrosurgical apparatus according to claim 6, further comprising a cold plasma probe connected to said second connector of said conversion unit.

9. An electrosurgical apparatus according to claim 6, wherein said connector for connecting a cold plasma probe comprises an electro-gas output connector.

10. An electrosurgical apparatus according to claim 6, further comprising an electrosurgical generator, wherein said first connector for connecting said conversion unit to an electrosurgical generator connects to a high-voltage output of said electrosurgical generator.

11. An electrosurgical apparatus according to claim 6, wherein said conversion unit further comprises a gas connector for connecting said conversion unit to a source of an inert gas.

12. An electrosurgical apparatus according to claim 6, wherein said conversion unit further comprises:
   a first insulation between primary coil and said secondary coil; and
   a second insulation between said primary and secondary coils and the core;
   wherein said first insulation is greater than said second insulation.

13. An electrosurgical system comprising:
   an electrosurgical generator;
   a source of inert gas;
   a cold plasma probe;
   a conversion unit comprising:
      a first connector connected to said electrosurgical generator;
      a high voltage transformer having a ferrite core, a primary coil of wire on said ferrite core and a secondary coil of wire on said core, said primary coil of wire having a first gauge and said secondary coil of wire having a second gauge, the secondary coil having a larger number of turns than the primary coil and said second gauge being smaller than said first gauge;
      a second connector connected to said source of an inert gas; and
      a third connector connected to said cold plasma probe.

14. An electrosurgical apparatus according to claim 13, wherein said conversion unit further comprises:
   a first insulation between primary coil and said secondary coil; and
   a second insulation between said primary and secondary coils and the core;
   wherein said first insulation is greater than said second insulation.

15. An electrosurgical apparatus according to claim 13, wherein said primary coil comprises 30 AWG magnetic wire and said secondary coil comprises 36 AWG magnetic wire.

16. An electrosurgical apparatus according to claim 13, wherein said a diameter of said primary coil is approximately twice the diameter of the secondary coil.

17. An electrosurgical apparatus according to claim 13, wherein said first number of turns comprises 25 turns and said second number of turns comprises 250 turns.

18. An electrosurgical apparatus according to claim 13, wherein said second number of turns is a multiple of said first number of turns.

* * * * *